United States Patent
Bloembergen et al.

(10) Patent No.: US 11,666,515 B2
(45) Date of Patent: Jun. 6, 2023

(54) PHOSPHATE CROSSLINKED STARCH NANOPARTICLE AND DENTAL TREATMENTS

(71) Applicant: GREENMARK BIOMEDICAL INC., East Lansing, MI (US)

(72) Inventors: Steven Bloembergen, Okemos, MI (US); Nathan A. Jones, Ann Arbor, MI (US)

(73) Assignee: GREENMARK BIOMEDICAL INC.

( * ) Notice: Subject to any disclaimer, the term of this patent is extended or adjusted under 35 U.S.C. 154(b) by 305 days.

(21) Appl. No.: 16/966,784

(22) PCT Filed: Mar. 28, 2019

(86) PCT No.: PCT/US2019/024619
§ 371 (c)(1),
(2) Date: Jul. 31, 2020

(87) PCT Pub. No.: WO2019/191456
PCT Pub. Date: Oct. 3, 2019

(65) Prior Publication Data
US 2021/0000710 A1    Jan. 7, 2021

Related U.S. Application Data

(60) Provisional application No. 62/648,986, filed on Mar. 28, 2018, provisional application No. 62/661,669, filed on Apr. 24, 2018.

(51) Int. Cl.
*A61K 8/21* (2006.01)
*A61K 8/02* (2006.01)
*A61K 8/19* (2006.01)
*A61K 8/55* (2006.01)
*A61Q 11/00* (2006.01)

(52) U.S. Cl.
CPC .............. *A61K 8/21* (2013.01); *A61K 8/0241* (2013.01); *A61K 8/19* (2013.01); *A61K 8/55* (2013.01); *A61Q 11/00* (2013.01)

(58) Field of Classification Search
CPC ...... C08B 31/04; C01F 220/00; C08F 251/00; A81K 9/51; A61K 47/36
IPC ........ A61K 8/21,8/19, 8/55, 8/02; A61Q 11/00
See application file for complete search history.

(56) References Cited

U.S. PATENT DOCUMENTS

| | | |
|---|---|---|
| 675,915 A | 6/1901 | Woods |
| 2,148,951 A | 2/1939 | Maxwell |
| 2,328,537 A | 9/1943 | Felton et al. |
| 2,425,058 A | 8/1947 | Craig |
| 2,500,950 A | 3/1950 | Konigsberg |
| 2,801,242 A | 7/1957 | Kerr et al. |
| 2,819,240 A | 1/1958 | De et al. |
| 2,824,099 A | 2/1958 | Craig |
| 2,929,811 A | 3/1960 | Hofreiter et al. |
| 2,989,521 A | 6/1961 | Senti et al. |
| 4,126,669 A | 11/1978 | Rothman et al. |
| 5,087,649 A | 2/1992 | Wegner et al. |
| 6,011,092 A | 1/2000 | Seppaelae et al. |
| 6,340,527 B1 | 1/2002 | Van Soest et al. |
| 6,379,494 B1 | 4/2002 | Jewell et al. |
| 6,677,386 B1 | 1/2004 | Giezen et al. |
| 6,749,868 B1 | 6/2004 | Desai et al. |
| 6,755,915 B1 | 6/2004 | Van Soest et al. |
| 6,825,252 B2 | 11/2004 | Helbling et al. |
| 6,921,430 B2 | 7/2005 | Bloembergen et al. |
| 7,550,441 B2 | 6/2009 | Farokhzad et al. |
| 8,043,480 B2 | 10/2011 | Lahann et al. |
| 8,048,453 B1 | 11/2011 | Sung et al. |
| 8,759,322 B2 | 6/2014 | Akiyoshi et al. |
| 9,133,279 B2 | 9/2015 | Perrier et al. |
| 10,285,943 B2 | 5/2019 | Bloembergen et al. |
| 2002/0136769 A1 | 9/2002 | Kabanov et al. |
| 2003/0219785 A1 | 11/2003 | Hallahan et al. |

(Continued)

FOREIGN PATENT DOCUMENTS

| | | | |
|---|---|---|---|
| EP | 0311873 A2 | 4/1989 | |
| EP | 1159301 B1 | 10/2003 | |

(Continued)

OTHER PUBLICATIONS

Alexiou et al., "Targeting Cancer Cells: Magnetic Nanoparticles as Drug Carriers," European Biophysics Journal, 2006, vol. 35(5), pp. 446-450.

Alonso et al., "Antimetastatic Effect of Desmopressin In a Mouse Mammary Tumor Model," Breast Cancer Research and Treatment, Oct. 1999, vol. 57 (3), pp. 271-275.

Alzate P., et al., "Micro and Nanoparticles of Native and Modified Cassava Starches as Carriers of the Antimicrobial Potassium Sorbate," Starch, 2016, vol. 68(11-12), pp. 1038-1047.

Amin et al., "Hydrogels as Potential Drug Delivery Systems," Scientific Research and Essay, Dec. 2009, vol. 3 (11), pp. 1175-1183.

Aravind et al., "Aptamer-Labeled PLGA Nanoparticles for Targeting Cancer Cells," Cancer Nano, 2012, vol. 3(1-6), pp. 1-12.

(Continued)

*Primary Examiner* — Walter E Webb

(57) ABSTRACT

A phosphorous compound such as STMP is used as a cross-linking agent while making a starch nanoparticle in an emulsion process. Negative charge of the nanoparticle is reduced or reversed by adding cations and/or cationizing the starch optionally while forming the nanoparticles. Anionic active agents, such as fluoride or fluorescein, are optionally incorporated into the nanoparticle during the formation process. For example, a fluoride salt can also be used, which promotes the crosslinking reaction while also providing fluoride in the nanoparticle. The retention of both calcium and fluoride in the nanoparticle is improved when both salts are used. Alternatively, the nanoparticle may be used without added calcium and/or fluoride. The nanoparticles may be useful for tooth remineralization, the treatment of dentinal hypersensitivity, to treat caries, or as a diagnostic agent to locate carious lesions.

16 Claims, 2 Drawing Sheets

(56) References Cited

U.S. PATENT DOCUMENTS

| | | | |
|---|---|---|---|
| 2004/0028745 | A1 | 2/2004 | Bouhadir et al. |
| 2004/0039042 | A1 | 2/2004 | Fleming |
| 2004/0126900 | A1 | 7/2004 | Barry et al. |
| 2004/0241382 | A1 | 12/2004 | Bloembergen et al. |
| 2005/0191359 | A1 | 9/2005 | Goldshtein et al. |
| 2006/0002852 | A1 | 1/2006 | Saltzman et al. |
| 2006/0292280 | A1 | 12/2006 | Soper et al. |
| 2007/0224280 | A1 | 9/2007 | Lillard et al. |
| 2008/0081074 | A1 | 4/2008 | Gu et al. |
| 2008/0233200 | A1 | 9/2008 | Sung et al. |
| 2008/0241257 | A1 | 10/2008 | Popescu et al. |
| 2009/0061010 | A1 | 3/2009 | Zale et al. |
| 2009/0117549 | A1 | 5/2009 | Tan et al. |
| 2009/0155409 | A1 | 6/2009 | Sexton et al. |
| 2009/0196831 | A1 | 8/2009 | Yang et al. |
| 2009/0226521 | A1 | 9/2009 | Smyth et al. |
| 2009/0312402 | A1 | 12/2009 | Contag et al. |
| 2010/0093659 | A1 | 4/2010 | Natunen et al. |
| 2010/0093933 | A1 | 4/2010 | Karagianni et al. |
| 2010/0143738 | A1 | 6/2010 | Bloembergen et al. |
| 2010/0166872 | A1 | 7/2010 | Singh et al. |
| 2010/0266491 | A1 | 10/2010 | Farokhzad et al. |
| 2010/0267802 | A1 | 10/2010 | Sullenger |
| 2010/0272639 | A1 | 10/2010 | Dutcher |
| 2011/0014296 | A1 | 1/2011 | Chen et al. |
| 2011/0038939 | A1 | 2/2011 | Lvov et al. |
| 2011/0042841 | A1 | 2/2011 | Wildi et al. |
| 2011/0244044 | A1 | 10/2011 | Rossi et al. |
| 2011/0244048 | A1 | 10/2011 | Amiji et al. |
| 2012/0003888 | A1 | 1/2012 | Lee et al. |
| 2012/0141551 | A1 | 6/2012 | Bloembergen et al. |
| 2015/0299431 | A1 | 10/2015 | Parcq et al. |
| 2017/0112949 | A1 | 4/2017 | Lahann et al. |

FOREIGN PATENT DOCUMENTS

| | | | | |
|---|---|---|---|---|
| EP | 1961769 | A1 | 8/2008 | |
| EP | 1303670 | B1 | 1/2010 | |
| EP | 1303667 | B1 | 10/2010 | |
| EP | 2251484 | B1 | 6/2017 | |
| GB | 1420392 | A | 1/1976 | |
| JP | 2002544335 | A | 12/2002 | |
| JP | 2004500438 | A | 1/2004 | |
| JP | 2005535604 | A | 11/2005 | |
| WO | 0040617 | A1 | 7/2000 | |
| WO | 0066090 | A1 | 11/2000 | |
| WO | 0069916 | A1 | 11/2000 | |
| WO | 0178786 | A2 | 10/2001 | |
| WO | 03010206 | A1 | 2/2003 | |
| WO | 03101425 | A2 | 12/2003 | |
| WO | 2005108471 | A1 | 11/2005 | |
| WO | 2007069272 | A2 | 6/2007 | |
| WO | 2008022127 | A2 | 2/2008 | |
| WO | 2008060575 | A2 | 5/2008 | |
| WO | 2009146147 | A2 | 12/2009 | |
| WO | 2010042823 | A1 | 4/2010 | |
| WO | 2010053140 | A1 | 5/2010 | |
| WO | 2010065750 | A1 | 6/2010 | |
| WO | 2010080557 | A1 | 7/2010 | |
| WO | 2010084088 | A2 | 7/2010 | |
| WO | WO2010084060 | * | 7/2010 | A61K 9/51 |
| WO | 2011071742 | A2 | 6/2011 | |
| WO | 2011155979 | A2 | 12/2011 | |
| WO | 2012075414 | A2 | 6/2012 | |
| WO | 2012162845 | A1 | 12/2012 | |
| WO | 2013081720 | A1 | 6/2013 | |
| WO | 2017070578 | A1 | 4/2017 | |

OTHER PUBLICATIONS

Barker et al., "The Synthesis and Characterization of a Novel Polysaccharide Hydrogel for Biomedical Applications Including the Treatment of Malignant Tumors and the Prevention of Metastatic Disease." Thesis, University of Tennessee at Knoxville, Aug. 2007, pp. i-viii and 1-142.

Bates et al., "Discovery and Development of the G-Rich Oligonucleotide AS1411 as a Novel Treatment for Cancer," Experimental and Molecular Pathology, Jun. 2009, vol. 86 (3), pp. 151-164.

Blank et al., "Systematic Evolution of a DNA Aptamer Binding to Rat Brain Tumor Microvessels," Journal of Biological Chemistry, May 2001, vol. 276 (19), pp. 16464-16468.

Bloembergen et al., "Biolatex Binders for Paper and Paperboard Applications," Journal of Pulp and Paper Science, Jan. 2010, vol. 36 (3), pp. 1-11.

Bloembergen et al., "Paper Binder Performance With Nanoparticle Biolatextm: Ecosynthetix Develops Ecosphere Biolatex for Replacement of Petroleum Based Latex Binders," ACFS, Montreal, Jun. 11-13, 2008.

Bloembergen, et al., "Specialty Biobased Monomers and Emulsion Polymers Derived from Starch," Presented to the PTS Advanced Coating Fundamentals Symposium, Munich, Germany, Oct. 11-14, 2010, pp. 1-19.

Canadian Patent Application No. 2,790,763, Office Action dated Apr. 30, 2020.

Canadian Patent Application No. 2,790,763, Office Action dated Jan. 12, 2021.

Canadian Patent Application No. 2,790,763, Office Action dated Aug. 6, 2019.

Canadian Patent Application No. 2,819,240, Examiner's Requisition dated Jan. 11, 2018.

Canadian Patent Application No. 2,819,240, Office Action dated Aug. 28, 2019.

Canadian Patent Application No. 2,819,240, Office Action dated May 8, 2020.

Canadian Patent Application No. 2,819,240, Office Action dated Sep. 26, 2018.

Corre et al., "Starch Nanoparticles: A Review," Biomacromolecules, May 2010, vol. 11 (5), pp. 1139-1153.

Dave et al., "Regenerable DNA-Functionalized Hydrogels for Ultrasensitive, Instrument-Free Mercury(II) Detection and Removal in Water," Journal of the American Chemical Society, Aug. 2010, vol. 132 (36), pp. 12668-12673.

Davis, "Microspheres and Drug Therapy: Pharmaceutical, Immunological and Medical Aspects", Elsevier, New York, NY, USA, Chapter 2, 1984, pp. 25-37.

El-Feky et al., "Utilization of Crosslinked Starch Nanoparticles as a Carrier for Indomethacin and Acyclovir Drugs," Journal of Nanomedicine & Nanotechnology, 2015, vol. 6(1); 1000254, pp. 1-8.

European Patent Application No. 11845209.3, Office Action dated Oct. 24, 2018.

European Patent Application No. 11845209, Extended European Search Report dated Mar. 7, 2017.

European Patent Application No. 11845209, Supplementary Partial European Search Report dated Jul. 29, 2016.

European Patent Application No. 11845209.3, Office Action dated Nov. 21, 2017.

Ex Parte Podack Patent Trial and Appeal Board Appeal No. 2014-006893, Nov. 14, 2016, pp. 1-14 and a title page (15 total sheets).

Farokhzad et al., "Nanoparticle-Aptamer Bioconjugates: A New Approach for Targeting Prostate Cancer Cells," Cancer Research, Nov. 2004, vol. 64 (21), pp. 7668-7672.

Farokhzad et al., "Nanoparticle-Aptamer Bioconjugates for Cancer Targeting," Expert Opinion on Drug Delivery, May 2006, vol. 3 (3), pp. 311-324.

Fishman et al., "Molar Masses and Sizes of Starches by High-Performance Size-Exclusion Chromatography With On-line Multi-Angle Laser Light Scattering Detection," Journal of Agricultural and Food Chemistry, Oct. 1996, vol. 44 (10), pp. 3182-3188.

Gu et al., "Targeted Nanoparticles for Cancer Therapy," Nano Today, Jun. 2007, vol. 2 (3), pp. 14-21.

Hamidi et al., "Hydrogel Nanoparticles in Drug Delivery," Advanced Drug Delivery Reviews, Dec. 2008, vol. 60 (15), pp. 1638-1649.

(56) References Cited

OTHER PUBLICATIONS

Heidel et al., "Cyclodextrin-Containing Polymers: Versatile Platforms of Drug Delivery Materials," Journal of Drug Delivery, 2012, vol. 2012, pp. 17.
Herr et al., "Aptamer-Conjugated Nanoparticles for Selective Collection and Detection of Cancer Cells," Analytical Chemistry, May 2006, vol. 78 (9), pp. 2918-2924.
International Patent Application No. PCT/US2011/063102, International Preliminary Report on Patentability and Writter Opinion dated Jun. 13, 2013.
International Patent Application No. PCT/US2011/063102, International Search Report dated Jul. 6, 2012.
International Patent Application No. PCT/US2012/056582, International Preliminary Report on Patentability and Writter Opinion dated Jun. 12, 2014.
International Patent Application No. PCT/US2012/056582, International Search Report dated Feb. 28, 2013.
Jain et al., "Effective Insulin Delivery Using Starch Nanoparticles as a Potential Trans-Nasal-Nucoadhesive Carrier," European Journal of Pharmaceutics, Jun. 2008, vol. 69 (2), pp. 426-435.
Jones, et al., "Targeted Starch Nanoparticles for Cancer Therapy", Design Symposium, Mar. 23, 2012.
Kaptein S.J.F., et al., "A Derivate of the Antibiotic Doxorubicin Is a Selective Inhibitor of Dengue and Yellow Fever Virus Replication In Vitro," Antimicrobial Agents and Chemotherapy, 2010, vol. 54(12), pp. 5269-5280.
Kawano et al., "Effects of Polyethylene Glycol Spacer Length and Ligand Density on Folate Receptor Targeting of Liposomal Doxorubicin in Vitro," Journal of Drug Delivery, 2011, vol. 2011, Article ID 160967, 6 pages.
Lai, et al., "AS1411 Aptamer-Conjugated Polymeric Micelle for Targetable Cancer Therapy," Nanotech Conference and Expo 2010, Anaheim, CA, Abstract, Jun. 21-24, 2010.
Lee et al., "Delivery of Liposomes Into Cultured KB Cells via Folate Receptor-Mediated Endocytosis," The Journal of Biological Chemistry, Feb. 1994, vol. 269 (5), pp. 3198-3204.
Lee et al., "Development of New Biobased Emulsion Binders," Presented At Papercon 2010, Talent, Technology And Transformation, Altanta, GA, May 2-5, 2010.
Ma et al., "Fabrication and Characterization of Citric Acid-modified Starch Nanoparticles/Plasticized-starch 2, Omposites," Biomacromolecules, 2008, vol. 9, pp. 3314-3320.
Mangalam et al., "Cellulose/DNA Hybrid Nanomaterials," Biomacromolecules, Mar. 2009, vol. 10 (3), pp. 497-504.
Milla et al., "PEGylation of Proteins and Liposomes: A Powerful and Flexible Strategy to Improve the Drug Delivery," Current Drug Metabolism, Jan. 2012, vol. 13 (1), pp. 105-119.
Mongelard et al., "AS-1411, A Guanosine-Rich Oligonucleotide Aptamer Targeting Nucleolin for the Potential Treatment of Cancer, Including Acute Myeloid Leukemia," Current Opinion in Molecular Therapeutics, Feb. 2010, vol. 12 (1), pp. 107-114.
Moore M.D., et al., "Generation of neutralizing aptamers against herpes simplex virus type 2: potential components of multivalent microbicides," The Journal of general virology, 2011, pp. 1493-1499.
Academy of Pediatrics (Helathychildren.Org; Jul. 11, 2017).
Bowen, et al., "The Stephan Curve Revisited," Odontology, 2012, vol. 101, pp. 2-8.
Canadian Patent Application No. 2,790,763, Office Action dated Feb. 21, 2022.
Canadian Patent Application No. 2,790,763, Office Action dated Jul. 23, 2021.
Canadian Patent Application No. 2,790,763, Office Action dated Sep. 25, 2018.
Chinese Patent Application No. 201980022325.0, Office Action dated May 25, 2022—English Translation available.
European Patent Application No. 19774807.2, Extended European Search Report dated Oct. 28, 2021.
Khiavi et al., "Therapeutic Efficacy of Orally Delivered Doxorubicin Nanoparticles in Rat Tongue Cancer Induced by 4-Nitroquinoline 1-Oxide," Advanced Pharmaceutical Bulletin, Jun. 2015, vol. 5 (2), pp. 209-216.
Shi et al., "Preparation of Starch-based Nanoparticles Through High-pressure Homogenization and Miniemulsion Cross-linking: Influence of Various Process Parameters on Particle Size and Stability," Carbohydrate Polymers, Feb. 1, 2011, vol. 83, pp. 1604-1610.
Simmons et al., "Anti-Heparanase Aptamers as Potential Diagnostic and Therapeutic Agents for Oral Cancer," PLoS One, 2014, vol. 9 (10), e96846.
U.S. Appl. No. 14/360,503, Notice of Allowance dated Apr. 4, 2022.
U.S. Appl. No. 13/486,555, Decision on Appeal dated Aug. 25, 2021.
U.S. Appl. No. 14/360,503 Notice of Allowance dated Feb. 25, 2022.
U.S. Appl. No. 14/360,503, Notice of Allowance dated Nov. 9, 2021.
U.S. Appl. No. 16/383,998, Non-Final Office Action dated Oct. 25, 2021.
U.S. Appl. No. 16/391,918, Final Office Action dated Jun. 29, 2021.
U.S. Appl. No. 16/391,918, Non Final Rejection dated May 27, 2022.
Behnan, et al. "In-vitro evaluation of various treatments to prevent demineralization next to orthodontic brackets", American Journal of Orthodontics and Dentofacial Orthopedics, Dec. 2010, pp. 712.e1-712.e7.
U.S. Appl. No. 14/360,503, Final Office Action dated Aug. 16, 2018.
U.S. Appl. No. 14/360,503, Final Office Action dated Sep. 9, 2016.
U.S. Appl. No. 14/360,503, Non-Final Office Action dated Jan. 22, 2016.
U.S. Appl. No. 14/360,503, Non-Final Office Action dated Nov. 24, 2017.
U.S. Appl. No. 14/360,503, Office Action dated Aug. 10, 2015.
U.S. Appl. No. 16/383,998, Final Office Action dated Mar. 24, 2020.
U.S. Appl. No. 13/310,287, Decision on Appeal dated Mar. 31, 2017.
Wang et al., "Superparamagnetic Iron Oxide Nanoparticle-Aptamer Bioconjugates for Combined Prostate Cancer Imaging and Therapy." ChemMedChem, vol. 3, 2008, pp. 1311-1315.
Wenz, "Cyclodextrine als Bausteine supramolekularer Strukturen und Funktionseinten," Angewandte Chemie, 1994, vol. 106, pp. 851-870.
Written Opinion for Application No. PCT/US2011/063102, dated Jul. 6, 2012, 8 pages.
Written Opinion for Application No. PCT/US2012/056582, dated Feb. 28, 2013, 9 pages.
Wu et al., "DNA Aptamer-Micelle as an Efficient Detection/Delivery Vehicle Toward Cancer Cells," Proceedings of the National Academy of Sciences of the United States of America, Jan. 2010, vol. 107 (1), pp. 5-10.
Xiao et al., "Preparation of Folate-Conjugated Starch Nanoparticles and its Application to Tumor-Targeted Drug Delivery Vector," Chinese Science Bulletin, Jul. 2006, vol. 51 (14), pp. 1693-1697.
Xiao et al., "Studies Of Poly-L-Lysine-Starch Nanoparticle Preparation And Its Application As Gene Carrier," Science in China Series B Chemistry, Mar. 2005, vol. 48 (2), pp. 162-166.
Yamada et al., "Design of Folate-Linked Liposomal Doxorubicin to Its Antitumor Effect in Mice," Clinical Cancer Research, Dec. 2008, vol. 14 (24), pp. 8161-8168.
Yang et al., "Investigation of Folate-Conjugated Fluorescent Silica Nanoparticles for Targeting Delivery to Folate Receptor-Positive Tumors and Their Internalization Mechanism," International Journal of Nanomedicine, 2011, vol. 6, pp. 2023-2032.
International Patent Application No. PCT/US2019/024619, International Search Report dated Jun. 27, 2019.
Anonymous, "The Influence of Zeta Potential", silvercolloids.com, Mar. 9, 2018, 1 page.
Jones et al., "Nanoparticle-Based Targeting and Detection of Microcavities", Advanced Healthcare Materials, vol. 6, Article No. 1600883, Nov. 15, 2016, p. 1-9.

(56) References Cited

OTHER PUBLICATIONS

International Patent Application No. PCT/US2019/024619, International Preliminary Report on Patentability dated Sep. 29, 2020.
Li, Bing-Zheng et. al. "Fabrication of starch-based microparticles by an emulsification-crosslinking method", Journal of Food Engineering 92 (2009) 250-254.
Li, Bing-Zheng et. al. "Physical properties and loading capacity of starch-based microparticles crosslinked with trisodium trimetaphosphate", Journal of Food Engineering 92 (2009) 255-260.
Nationwide Children's Hospital, Herpes Simplex Virus (HSV), Jun. 1993. pp. 1-2.
Ozalp et al., "Aptamer-Gated Nanoparticles for Smart Drug Delivery," Pharmaceuticals, 2011, vol. 4 (8), pp. 1137-1157.
Peng et al., "Targeted Magnetic Iron Oxide Nanoparticles for Tumor Imaging and Therapy," International Journal of Nanomedicine, 2008, vol. 3 (3), pp. 311-321.
Phillips et al., "Applications of Aptamers in Cancer Cell Biology," Analytica Chimica Acta, Jul. 2008, vol. 621 (2), pp. 101-108.
Rupendra Mukerjea, Giles Slocum and John F. Robyt. "Determination of the maximum water solubility of eight native starches andthe solubility of their acidic-methanol and -ethanol modified analogues." Carbohydrate Research, vol. 342 (2007) pp. 1 03-110. (Year: 2007).
Saboktakin et al., "pH-sensitive Starch Hydrogels via Free Radical Graft Copolymerization, Synthesis and Properties," Carbohydrate Polymers, Jul. 2009, vol. 77 (3), pp. 634-638.
Saenger, "Cyclodextrin-Einschubverbindungen in Forschung Ung Industrie," Angewandte Chemie, 1980, vol. 92, pp. 343-361.
Sasaki et al., "A Combination of Desmopressin and Docetaxel Inhibit Cell Proliferation and Invasion Mediated by Irokinase-type Plasminogen Activator (uPA) in Human Prostate Cancer Cells," Biochemical and Biophysical Research communications. Aug. 2015, vol. 464 (3), pp. 848-854.
Shangguan et al., "Aptamers Evolved from Cultured Cancer Cells Reveal Molecular Differences of Cancer Cells in Patient Samples," Clinical Chemistry, Jun. 2007, vol. 53 (6), pp. 1153-1155.
Shangguan et al., "Aptamers Evolved From Live Cells as Effective Molecular Probes for Cancer Study," Proceedings of the National Academy of Sciences, Aug. 2006, vol. 103 (32), pp. 11838-11843.
Shangguan et al., "Aptamers Evolved From Live Cells as Effective Molecular Probes for Cancer Study," Proceedings of the National Academy of Sciences of the United States of America, Aug. 2006, vol. 103 (32), pp. 11838-11843.
Shin et al., "Rheological Properties of Starch Latex Dispersions and Starch Latex-containing Coating Colors," Presented at PaperCon 2012, "Growing the Future", New Orleans, LA, Apr. 21-25, 2012, pp. 1-26.
Simi et al., "Hydrophobic Grafted and Cross-linked Starch Nanoparticles for Drug Delivery," Bioprocess and Biosystems Engineering, May 2007, vol. 30 (3), pp. 173-180.
Song et al., "Starch Nanoparticle Formation via Reactive Extrusion and Related Mechanism Study," Carbohydrate Polymers, Apr. 2011, vol. 85 (15), pp. 208-214.
Soontornworajit et al., "Aptamer-Functionalized in Situ Injectable Hydrogel for Controlled Protein Release," Journal of Biomacromolecules, Sep. 1, 2010, vol. 11 (10), pp. 2724-2730.
Soundararajan et al., "Plasma Membrane Nucleolin is a Receptor for an Anticancer Aptamer AS1411 in MV4-11 Leukemia Cells," Molecular Pharmacology, Nov. 2009, vol. 76 (5), pp. 984-991.
Stuart et al., "Randomized Phase II Trial of the Nucleolin Targeting Aptamer AS1411 Combined with High-Dose Cytarabine in Relapsed/Refractory Acute Myeloid Leukemia (AML)," Journal of Clinical Oncology, 2009, vol. 27 (15s), pp. 7019.
Suk et al., "PEGylation as a Strategy for Improving Nanoparticle-Based Drug and Gene Delivery," Advanced Drug Delivery Reviews, Apr. 2016, vol. 99 (Pt A), pp. 28-51.
Thapa et al., "Folate-PEG Conjugates of a Far-Red Light-Activatable Paclitaxel Prodrug to Improve Selectivity Toward Folate Receptor-Positive Cancer Cells" ACS Omega, Oct. 2017, vol. 2(10), pp. 6349-6360.
Thiele et al., "Nanoparticle of Anionic Starch and Cationic Cyclodextrin Derivatives for the Targeted Delivery of Drugs," Polymer Chemistry, Oct. 2010, vol. 2 (1), pp. 209-215.
U.S. Appl. No. 13/990,278, Non-Final Office Action dated Sep. 13, 2018.
U.S. Appl. No. 16/391,918, Restriction Requirement dated Mar. 20, 2020.
U.S. Appl. No. 16/383,998, Non-Final Office Action dated Jul. 2, 2020.
U.S. Appl. No. 16/383,998, Final Office Action dated Nov. 10, 2020.
U.S. Appl. No. 16/383,998, Non-Final Office Action dated Apr. 16, 2021.
U.S. Appl. No. 16/391,918, Non-Final Office Action dated Sep. 4, 2020.
U.S. Appl. No. 13/990,278, Non-Final Office Action dated Jul. 23, 2018.
U.S. Appl. No. 13/310,287, Examinees Answer to Appeal Brief dated Aug. 6, 2015.
U.S. Appl. No. 13/310,287, Office Action dated Apr. 3, 2014.
U.S. Appl. No. 13/310,287, Office Action dated Jul. 18, 2013.
U.S. Appl. No. 13/310,287, Office Action dated Jul. 21, 2014.
U.S. Appl. No. 13/310,287, Office Action dated Jul. 5, 2012.
U.S. Appl. No. 13/310,287, Office Action dated Jun. 16, 2014.
U.S. Appl. No. 13/310,287, Office Action dated Nov. 21, 2012.
U.S. Appl. No. 13/310,287, Office Action dated Oct. 31, 2013.
U.S. Appl. No. 13/614,120, Office Action dated Apr. 4, 2014.
U.S. Appl. No. 13/614,120, Office Action dated Feb. 7, 2013.
U.S. Appl. No. 13/614,120, Office Action dated Jul. 24, 2014.
U.S. Appl. No. 13/614,120, Office Action dated Jul. 29, 2013.
U.S. Appl. No. 13/614,120, Office Action dated Jun. 13, 2014.
U.S. Appl. No. 13/614,120, Office Action dated Dec. 8, 2014.
U.S. Appl. No. 13/990,278, Final Office Action dated Jan. 22, 2018.
U.S. Appl. No. 13/990,278, Non-Final Office Action dated Jun. 14, 2017.
U.S. Appl. No. 13/990,278, Non-Final Office Action dated Nov. 23, 2016.
U.S. Appl. No. 13/990,278, Notice of Allowance dated Jan. 15, 2019.
U.S. Appl. No. 13/990,278, Notice of Allowance dated Mar. 30, 2018.
U.S. Appl. No. 13/990,278, Office Action dated Aug. 3, 2015.
U.S. Appl. No. 13/990,278, Office Action dated Mar. 20, 2014.
U.S. Appl. No. 13/990,278, Office Action dated May 5, 2016.
U.S. Appl. No. 13/990,278, Office Action dated Oct. 9, 2015.

* cited by examiner

PHOSPHATE CROSSLINKED STARCH NANOPARTICLE AND DENTAL TREATMENTS

RELATED APPLICATIONS

This application is a National Stage Entry of International Application No. PCT/US2019/024619, filed Mar. 28, 2019, which claims priority from and/or the benefit of U.S. provisional application 62/648,986 filed on Mar. 28, 2018 and U.S. provisional application 62/661,669 filed on Apr. 24, 2018, both of which are incorporated by reference.

FIELD

This specification relates to biopolymer nanoparticles, for example nanoparticles containing phosphorous and optionally one or more of calcium and fluorine (i.e. fluoride), and to methods of making the nanoparticle. The specification also relates to dental diagnostic and therapeutic treatments, for example the identification of carious lesions, tooth remineralization, treatment of carious lesions, or treatment of dentinal hypersensitivity.

BACKGROUND

International Publication Number WO 2017/070578, Detection and Treatment of Caries and Microcavities with Nanoparticles, describes nanoparticles for detecting and/or treating active carious lesions or microcavities in teeth. The nanoparticle comprises starch bearing at least one cationic region and/or having a net positive charge and thereby capable of associating with carious lesions on a tooth. In some examples the nanoparticles comprise an anticaries agent or a remineralizing agent. In some examples, the nanoparticles are formed from starch by a reactive extrusion process as described in U.S. Pub. No. 2011/0042821. After the nanoparticles are formed, they are cationized and fortified with a fluoride-containing component, a calcium-containing component or a calcium and phosphate-containing component by lyophilization. The nanoparticles have a positive zeta potential at the pH of saliva. In one example, an anionic fluoride salt was loaded into cationic starch nanoparticles. A 30-minute delay in the release of fluoride in artificial saliva through a dialysis membrane was observed for the nanoparticles relative to a reference solution of free fluoride salt.

INTRODUCTION

The following section is intended to introduce the reader to the invention and the detailed description to follow but not to limit or define any claimed invention.

Dental caries (tooth decay) is the most prevalent chronic disease in the world. Nearly everyone will develop caries at some point in their life. At any given time 42% of children and 25% of adults have untreated caries, leading to complications ranging from pain, infection, poor quality of life and in rare cases, death. Globally it is estimated that over $200 billion is spent annually on the management of this disease and its complications. Surgical treatment results in an irreversible restorative cycle leading to several replacement restorations, crowns and eventually tooth loss or dental implants as patients age. Carious lesions initially form when bacteria in the dental biofilm ferment sugars and produce organic acids, which demineralize enamel. As minerals leach from enamel rods, the area becomes more porous and weakens. The early lesion is comprised of a surface layer (surface zone) which appears relatively unaffected by the carious attack compared to the subsurface (lesion body). The surface zone results from mineral precipitation and is explained by solubility gradients, dissolution/precipitation mechanisms and protection by adsorbed agents present in saliva. Reports indicate that the carious lesion body has a pore volume (measure of porosity) of 5-30% and the surface zone <5%, compared to sound enamel which has a pore volume of 0.1%. These areas of subsurface porosity present clinically as a milky white opacity known as a "white spot lesion", and identify early stage caries to the clinician. If the process is not reversed, tiny open microchannels in the enamel surface allow acid to continue entering the subsurface. The lesion thus becomes more and more porous, until it eventually cavitates, requiring invasive surgical restoration (dental filling). However, the caries process is dynamic and early stage caries is sometimes reversible with better hygiene and remineralization agents such as high fluoride treatments or toothpastes. Some caries become inactive or "arrested" naturally and do not require any treatment, because the porosity particularly on the surface has been reduced by mineral and/or protein deposition. A better understanding of the caries process is leading to a paradigm shift in caries management, which emphasizes enamel preservation and minimally invasive dentistry, leading to better oral health outcomes. However, there is a need for alternative and/or improved remineralization agents.

Dental caries and other remineralized areas of a tooth are negatively charged and often found near plaque, which may also be negatively charged. Phosphorous and calcium are lost when a tooth demineralizes and phosphorous-calcium minerals are useful when remineralizing a tooth. Fluoride is also useful for remineralizing teeth and in the prevention or treatment of caries.

In a process described herein, a phosphorous compound such as STMP is used as a cross-linking agent while making a starch nanoparticle. The cross-linking agent thereby provides a useful element but STMP crosslinked nanoparticles have a negative charge and can be expected to be repelled from caries by electrostatic forces. However, as described herein, the negative charge can be at least reduced, and optionally neutralized or reversed, by adding preferably multi-valent cations and/or cationizing the starch, one or both of which may be done optionally while forming the nanoparticles. The addition of a calcium salt in particular serves to make the charge of the nanoparticle more suitable for targeting to caries while also providing another element, calcium, that is useful for remineralizing teeth. The addition of cations such as calcium also appears to increase the retention of anionic active agents, such as fluoride or fluorescein, which may also be incorporated into the nanoparticle during the formation process. Fluoride can usefully react to form minerals in the mouth, or to form minerals with calcium and/or phosphorous in the nanoparticle that can be delivered to a tooth. Further, a fluoride salt can be used to increase the ionic strength of the water phase in the nanoparticle formation process, which may promote the cross-linking reaction while also providing fluoride in the nanoparticle. While it is not necessary to add either or both of the calcium salt and the fluoride salt, the retention of both calcium and fluoride in the nanoparticle is improved when both salts are used. Alternatively, the nanoparticle may be used without added calcium and/or fluoride. A nanoparticle with phosphate compounds as its only remineralizing agents, with the starch cationized such that the nanoparticle has a positive zeta potential at pH of 5.5 and under, is also shown to be useful for remineralization. Given that active carious lesions generally have a pH below 5.5, without intending to be limited by theory, it is expected that the aforementioned nanoparticle would be beneficial for targeting into the carious lesions, or for pH-triggered targeting if the nanoparticle optionally has a negative zeta potential at a pH of 7 and above. In addition to remineralization, various nanoparticles described herein may be used for the treatment of dentinal hypersensitivity, to help prevent or treat caries, or as a diagnostic agent to locate carious lesions.

This specification describes methods of making starch based nanoparticles made with a phosphate crosslinker according to an emulsion process, and the resulting starch nanoparticles with one or more phosphates. Optionally, the nanoparticles have an anionic active agent, which may be added while making the nanoparticles. Optionally, the nanoparticles have a cation, which may be an active agent, and/or cationic moieties on the starch. The cation and/or cationic moieties may be added while making the nanoparticles. The nanoparticles may be used in one or more methods of diagnostic or therapeutic treatment such as the identification of carious lesions, tooth remineralization, treatment of carious lesions, or treatment of dentinal hypersensitivity.

In various processes described herein, starch based nanoparticles are made using an emulsion process such as a phase inversion emulsion process. The biopolymer is cross-linked with a phosphate cross-linker, for example STMP. Optionally, one or more of (i) a multivalent cation, such as calcium, (ii) an ionic active agent, such as fluorine (i.e. fluoride) and/or fluorescein, and (iii) one or more starch cationizing agents, are present in the water phase of a water-in-oil emulsion. Compounds may be added to the water phase while the water phase is emulsified (i.e. after phase inversion), during the phase inversion, or before the water phase is emulsified (i.e. before phase inversion). The water phase also contains the starch and phosphate cross-linker. In some examples, a fluoride salt and/or a fluorescein salt is added to the water phase before phase inversion. In some examples, a calcium salt and/or one or more starch cationizing agents are added to the water phase during or after phase inversion.

Various nanoparticles described herein comprises starch, phosphorous and optionally one or more active agents such as calcium, fluorine (i.e. fluoride) and fluorescein.

The phosphorous may include one or more starch-phosphate compounds and/or dangling phosphates. Optionally, the nanoparticles have a positive zeta potential at a pH of 5.5 or less. Optionally, the nanoparticles may have a negative zeta potential at a pH of 7.0 or more. Optionally, the nanoparticles may have a size in the range of 100-700 nm or 100-500 nm as determined by the peak intensity or Z-average size in dynamic light scattering (DLS) or as determined by the mean size or D50 in nanoparticle tracking analysis (NTA).

This specification also describes a method of providing one or more elements to a tooth, and the use of a nanoparticle to provide one or more elements to a tooth. Optionally, the elements are delivered to the tooth in the form of one or more minerals which may be insoluble in saliva at least at ordinary pH, for example 6.2 to 7.6. Optionally, the elements are delivered to a tooth as ions or in salts or other compounds that are soluble in saliva at ordinary pH. Optionally, phosphorous is delivered to a tooth as part of one or more phosphorous-starch compounds. The nanoparticles may be delivered to the tooth by way of attachment to plaque on the tooth or by way of attachment to and/or entry into a carious lesion.

This specification also describes the use of nanoparticles to treat a tooth, or a method of treating a tooth. The method includes applying nanoparticles to a tooth. The treatment may provide, for example, one or more of identification of a carious lesion, remineralization, treatment of a carious lesion and treatment of dentinal hypersensitivity.

Nanoparticles as described herein can be used to carry phosphorous and optionally calcium and/or fluorine (i.e. fluoride) to a demineralized region of a tooth. The nanoparticles can be applied, for example, by rinsing the mouth with an aqueous dispersion of the nanoparticles. Alternatively, a gel or paste having dispersed nanoparticles therein can be applied to a tooth. Optionally, some or all of the plaque and/or pellicle can be removed from a tooth before or during the application of the nanoparticles, which may help the nanoparticles attach to a carious surface of the tooth or to enter into pores of the tooth.

However, the removal of pellicle is optional even when targeting carious lesions. Alternatively, plaque may be left in place and the nanoparticles may be targeted to the plaque.

Without intending to be limited by theory, it is expected that the nanoparticles will help deliver one or more elements to a demineralized area of a tooth by one or more of: increasing the concentration of an element in a rinse, gel or paste relative to a solution or non-nanoparticle dispersion containing the element; targeting the elements to a demineralized area or associated plaque with or without entry of the nanoparticle into a pre-carious lesion; carrying minerals that can act as seed crystals, bio-active compounds or filling material; providing one or more elements for reaction with elements released from a tooth or present in saliva; or, providing a delayed or sustained release of one or more elements.

DETAILED DESCRIPTION

Figure 1:
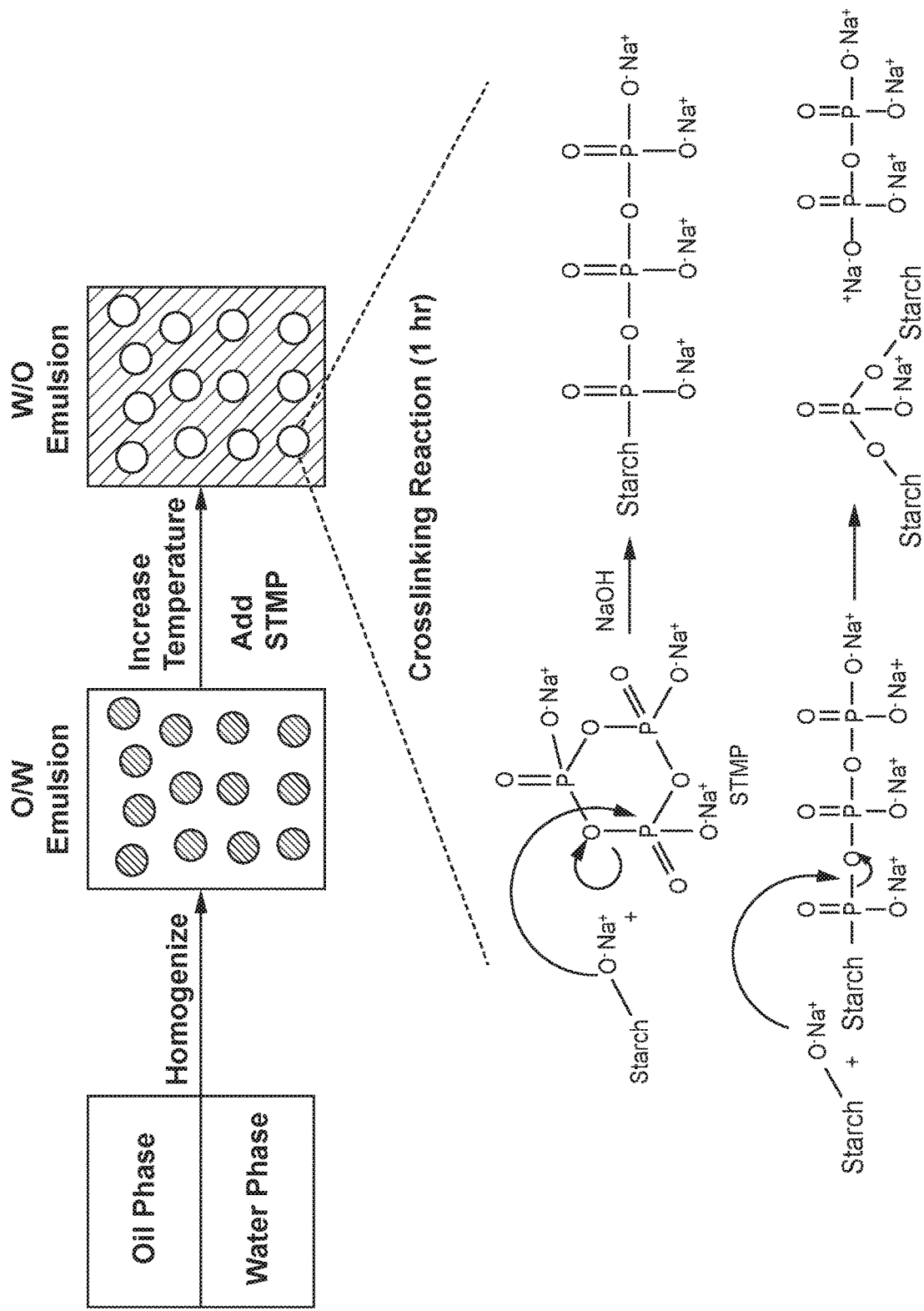
FIG. 1 is a schematic process flow diagram of biopolymer nanoparticle formation by way of phase inversion emulsion.

Dental cavities begin with one or more areas of demineralization that present as a white spot. The white spot can alternatively be called a pre-cavity, a pre-carious lesion or a white spot lesion. The enamel of the white spot has greater porosity than natural enamel due to erosion typically caused by oral bacteria that release acids. The enamel surface may remain intact, but in an active lesion open micropores allow acid to penetrate into the tooth. The area of the white spot thus becomes more and more porous and demineralized over time. Eventually the white spot area may become so weak that the enamel surface collapses and a cavity is formed. In this specification, references to demineralized areas of the tooth include white spots and cavities unless a particular type of demineralized area is specified. However, it is expected that the nanoparticles described herein will be particularly useful in treating white spots where it is difficult or damaging to access the porous structure by conventional means. For example, conventional topically applied fluoride solutions may merely seal the surface of the white spot, thus making the white spot inactive but not restore the dominant porous area underneath the surface. Drilling the tooth to provide fillings or bio-active materials removes some of the natural enamel which is then lost forever, as it cannot reform at this stage. The nanoparticles described herein may be targeted to the white spots themselves or to plaque that may be near the white spots. The nanoparticles described herein may also be useful in occluding or sealing pores in dentin, as in the treatment of dentinal hypersensitivity. It is expected that treatment with the nanoparticles will be most beneficial when the white spot is in a pre-cavitated stage and active with open micropores and subsurface porosity. However, treatment with the nanoparticles may also be done after a cavity (hole) is formed in more advanced stages of caries.

Without intending to be limited by theory, the inventors believe that as calcium leaches away from a demineralized area of a tooth, it leaves behind negative polyphosphate charges in the interior of the tooth. Nanoparticles can enter the demineralized area through micropores in an active lesion. The concentration of useful elements loaded into a nanoparticle dispersion might exceed the concentration of a comparable solution of the same elements. If the nanoparticles are positively charged, they may also associate with the surface (including surfaces below the outer enamel surface) of a tooth or plaque as a result of electrostatic attraction, thereby increasing either the delivery or retention, or both, of elements in the nanoparticle. Once on or inside the tooth, saliva degrades the biopolymers and one or more elements and/or minerals released by the nanoparticle can help restore the pores and/or subsurface area. Materials delivered by the nanoparticles may, for example, react with ions or compounds of the tooth or saliva, provide seed particles for mineral formation, act as a bioactive compound that can be incorporated into naturally produced minerals, or simply fill the demineralized subsurface area.

In a method described herein, biopolymer, i.e. starch, nanoparticles are made using an emulsion process. In brief, one or more biopolymers are dispersed or dissolved in water, the water is then dispersed (i.e. emulsified) in another phase, for example an oil phase, and the biopolymer is crosslinked while in dispersed droplets of the water phase in the dispersion or emulsion. The use of an oil as a second phase is optional but helps to load water-soluble reactants into the droplets of the water phase. However, another non-solvent of starch, for example ethanol or hexane, or a multi-phase aqueous system, may be used. The crosslinker may be a phosphate or polyphosphate crosslinker such as sodium trimetaphosphate (STMP) or sodium tripolyphosphate (STTP).

Optionally, the process may be a phase inversion emulsion (PIE) process. A schematic of a phase inversion process is shown in FIG. 1. In the example illustrated, a starch-based nanoparticle is made with a sodium trimetaphosphate (STMP) crosslinker. Initially an oil-in-water emulsion is formed which, after an increase in temperature, becomes a water-in-oil emulsion. A surfactant may be used to assist in the oil-in-water to water-in-oil transition and to select the temperature at which this transition occurs. The STMP is added so that the crosslinking reaction occurs within water droplets of the water-in-oil emulsion. Additional elements may be added to the water phase by adding them at any of the three stages shown in FIG. 1 (separate water and oil phases, oil in water emulsion, water in oil emulsion).

Referring to FIG. 1, an oil phase is homogenized with a water phase containing dissolved starch or dispersed starch nanoparticles. The oil may be, for example, paraffin oil or a food grade mineral oil. Alternatively, other food grade oils such as sunflower oil or olive oil may be used. After forming an oil in water emulsion, the temperature is increased to more than the phase inversion temperature (PIT) for the reaction conditions. The PIT may vary depending on the ratio of water to oil, the presence and type of any surfactants (for example Tween 85), the presence and type of any catalysts (for example NaCl) and the type of oil. In some cases, the PIT may be in the range of 25-60° C. Optionally, heating can be provided by the high shear mixer itself, for example by increasing the mixer speed to heat the mixture. As the water in oil emulsion is being heated or after the phase inversion is complete, the crosslinker is added. The reaction may then continue, for example for about an hour.

The biopolymer is crosslinked using a phosphate crosslinker such as STMP, typically under alkaline conditions. While other crosslinkers might be used, STMP is advantageously available in food grade preparations. The crosslinker provides a source of phosphorus, an element useful for restoring a demineralized tooth. Part of the crosslinker (the inventors believe the part to be about 10-50% or 10-30%) reacts to form internal non-reversible (i.e. covalently bonded) crosslinks within the nanoparticles by way of monophosphate linkage. However, in addition to distarch monophosphate, side reactions may form other compounds such as monostarch triphosphate, monostarch monophosphate. The reaction is somewhat inefficient but dangling phosphate groups in either inorganic or organic compounds produced in the reaction or side reactions are available to form a strong associative complex with calcium and/or fluoride either within the particle or later when deployed in the oral cavity.

In some examples, NaCl salt is used to provide high ionic strength in the water phase, which favors the STMP reaction to occur in a subsequent step. However, in other examples described herein, NaF is used in place of, or in combination with, NaCl and to also provide fluoride in the nanoparticle. The NaF can be added, for example, in the water phase produced prior to homogenizing to form the O/W emulsion in FIG. 1. Alternatively, the NaF can also be added while homogenizing to form the O/W emulsion or after formation of the O/W emulsion or, though with a possible decrease in fluoride release time, after nanoparticle formation. In some examples, a calcium salt such as calcium chloride is added in the water phase. Optionally, the calcium salt, dry or in aqueous solution, is added into the W/O emulsion of FIG. 1 after the STMP is added or, possibly with some decrease in calcium and/or fluoride release time, after nanoparticle formation. Water soluble components are driven into the water droplets and at least partially react or otherwise associate with the nanoparticles. In another option, a calcium salt such as calcium chloride can be added in the water phase produced prior to homogenizing to form the O/W emulsion in FIG. 1 either in place of NaF and NaCl or in addition to NaF and/or NaCl. STMP produces negative charges in the resulting nanoparticle. The addition of calcium can block some of these charges. However, an additional step such as cationization of the starch is typically required to produce nanoparticles that are positively charged at neutral pH or even an acidic pH (i.e 5.5 or less) that may be found within or near a carious lesion.

The fluoride and/or calcium are present with the phosphorous and biopolymer in a dispersion of small water droplets in an emulsion, for example a water-in-oil emulsion, optionally stabilized by surfactant. Each droplet containing biopolymer produces a crosslinked particle. Optionally, an emulsion of water in another phase may be used.

The emulsion or emulsions are preferably produced using an ultra-high shear mixer, for example a Silverson dissolver agitator. This mixer advantageously produces minimal air encapsulation and provides sufficient shear to produce nanoparticles averaging under 700 nm or under 500 nm in diameter most of which, considering their hydrogel nature and distributions in the sizes of the nanoparticles and pores, are able to enter the pores of carious lesions (which average 750-800 nm in size). The starch may be cooked, chemically degraded and/or thermo-mechanically processed to help produce a solution or dispersion of starch in the water phase. Alternatively, smaller starch nanoparticles (20-200 nm) such as those produced by EcoSynthetix Inc. under the trademark EcoSphere™ can be used as the starch feed source. The resultant nanoparticles may have a mean or average size, measured for example by the peak in a dynamic light scattering (DLS) plot, the Z-average size (or harmonic intensity averaged particle diameter as described in ISO 13321 or ISO 22412) of a DLS measurement, or the mean or D50 value in a nanoparticle tracking analysis (NTA) measurement, of less than 1000 nm, for example 100-700 nm, 100-500 nm, 200-500 nm or 200-400 nm. After breaking the emulsion, the water phase can optionally be centrifuged, for example at 4000 rpm for 1 minute, to separate the nanoparticles in the supernatant from unassociated precipitates in the pellet. The nanoparticles are optionally washed to remove traces of oil although if a suitable, i.e. food-grade, oil is used it is not necessary to completely remove all traces of oil. The supernatant can be freeze dried to obtain dry nanoparticles. The nanoparticles can be stored dry or, for a more limited time, in an aqueous dispersion, gel or paste. An aqueous dispersion gel or paste can optionally be sterilized or stabilized with a biocide, antimicrobial preservative or biostatic additive.

The amount of cross-linker used may be 1% to 50 mol % of STMP based on anhydrous glucose repeating units (AGU). Preferred samples were produced with 3% to 50% STMP, or from 10% to 50% STMP, for example about 30% STMP. Particle size does not appear to be clearly related to the amount of STMP except that, in some examples, very low amounts of STMP (i.e. 1%) produced very small nanoparticles (about 100 nm), low amounts of STMP (i.e. 1-5%) produced large nanoparticles (average size of about 300-500 nm) while larger amounts of STMP (5% to 50%) produced intermediate nanoparticles (about 100-300 nm). Without intending to be limited by theory, it is possible that samples made with very low STMP (i.e. 1%) do not incorporate substantially all of the available starch into nanoparticles although 3% STMP seems to be sufficient. Once sufficient crosslinker is available, the smaller size with larger amounts of STMP may be due to higher crosslinking and less swelling (as predicted by the Stokes-Einstein equation related to volume swell ratio) since the particles are hydrogels and their size is measured in a swollen state. It is also possible that particle size is influenced more by the amount of shear energy applied or other factors that could affect droplet size of the water in oil emulsion. In some cases, nanoparticles made with added calcium had zeta potentials near neutral, for example in a range from −5 to +5 mV at a pH of 7.0. Optionally, precipitates produced in the water phase that are not associated with the nanoparticles can be separated by centrifugation. The nanoparticles tend to remain in the supernatant of the centrifuged sample. The nanoparticles exhibit swelling behavior and appear to be hydrogels. For example, the nanoparticles retain water, but the amount of water retained by the nanoparticles decreases with increasing ion concentration.

The nanoparticles become more negatively charged (as measured by zeta potential) with increasing pH and STMP content. In some examples, the zeta potential of nanoparticles with 1-50 mol % AGU of STMP, without calcium salt added and without starch cationization, ranged from 0 to −65 mV across a range of pH and STMP content, or −10 to −22 mV at neutral pH. For example, samples made with 30% STMP, without calcium salt added and without starch cationization, were measured as having a zeta potential of −15 mV at a pH of 3, −45 mV at pH of 8, and further decreasing to −70 mV at pH of 12.

Adding calcium, for examples as $CaCl_2$, but still without starch cationization (as described in more detail below) reduces the negative zeta potential of the nanoparticles. At near neutral pH and a 5% STMP content, the charge of the nanoparticles with calcium added can be in the range of −5 mV to 0 mV. Nanoparticles made with calcium and 30% STMP have a zeta potential in the range of −30 mV to −25 mV near neutral pH and without starch cationization. Without intending to be limited by theory, the added calcium may be capping the phosphate groups provided by the STMP. Optionally, the starch may be cationized to produce a further decrease in negative zeta potential, or to produce a positive zeta potential over a desired range of pH.

As an alternative to STMP, sodium tripolyphosphate (STTP) may be used as the crosslinker.

Optionally, the nanoparticles can be cationized, for example by the method described in International Publication Number WO 2017/070578, Detection and Treatment of Caries and Microcavities with Nanoparticles. Optionally, the starch may be cationized while in the water in oil emulsion. For example, glycidyl trimethyl ammonium chloride (GTAC), optionally with or pre-mixed with water and isopropyl alcohol or 2-proponol, may be added to the water phase before or after forming the water in oil emulsion. Alternatively, the starch may be cationized after the nanoparticles are formed. Alternatively, the starch may be cationized before the nanoparticles are formed, although in this case the starch is preferably first cooked or regenerated so that the cationization is not limited to the surface of the starch granules.

Optionally, a fluorophore could be added to the nanoparticles, for example by the method described in International Publication Number WO 2017/070578, Detection and Treatment of Caries and Microcavities with Nanoparticles. Alternatively, a fluorophore can be added during the formation of the nanoparticles, for example by adding the fluorophore to the water phase. Optionally, the nanoparticles could be co-dispersed with fluorescent cationic nanoparticles, for example nanoparticles described in International Publication Number WO 2017/070578, Detection and Treatment of Caries and Microcavities with Nanoparticles.

The incorporation of $PO_4^{3-}$, $Ca^{2+}$ and $F^-$ ions (as appropriate) into various samples containing phosphate only; phosphate and calcium only; and, phosphate, calcium and fluoride, was confirmed by energy-dispersive X-ray spectroscopy (EDX/EDS) used for elemental analysis of areas on SEM images.

The ion content of various freeze dried samples (moisture content less than 0.1%) was also measured by inductively coupled plasma (ICP) analysis. The phosphorous content of the nanoparticles increases with the amount of STMP used. The increase in phosphorous content increases generally linearly with STMP mol %. In one example, nanoparticles produced with from 1-50 mol % AGU of STMP had phosphorous contents ranging from about 1000 to about 21,000 ppm. In this example, phosphorous content was determined by ICP-MS after dialyzing the samples for 6 days and treating the samples with HCl and $HNO_3$. The phosphorous content values relate to total phosphorous, which is believed to be phosphorous bound to the nanoparticles, but the type of phosphate species present was not determined. Optionally, the range of STMP may be 3-50 mol % AGU or 10-50 mol % AGU, which gives 4,000-21,000 ppm phosphorous in the nanoparticle. Optionally, the range of STMP may be 20-40%, 25-35%, or about 30 mol % AGU.

For example, nanoparticles produced with 30 mol % AGU of STMP but without being cationized contained about 15,000 ppm of phosphorous. With 67 mol % dry $CaCl_2$) based on starch (anhydro-glucose repeating units) added, the nanoparticles also contained about 1,320,000 ppm calcium. With 70 mol % NaF and 67 mol % $CaCl_2$) (based on starch) also added, the nanoparticles contained 19,000 ppm fluoride and calcium content increased to 2,160,000 ppm. With 70 mol % NaF (based on starch) added without $CaCl_2$) (based on starch), the nanoparticles contained about 700 ppm fluoride.

The results above indicate that fluoride retention increases when calcium is also added and that calcium retention increases when fluoride is added. Calcium is believed to interact with phosphate through ionic interactions. Without intending to be limited by theory, it is possible that fluoride can co-precipitate with phosphate and calcium to form fluorapatite ($Ca_5(PO_4)_3F$) or other minerals in the nanoparticle. It is not clear if any of the calcium or fluoride is reacted with the starch or phosphates attached to the starch or not, or how the calcium or fluoride are combined with the starch. However, the phosphorous, calcium and fluoride contents described herein are measured in nanoparticles extracted from the supernatant of a centrifuged sample, wherein precipitates not bound to the nanoparticles were collected in the pellet of the centrifuge and not part of the measured calcium or fluoride contents. While no separation is perfect (and so some unbound precipitates might still be in the nanoparticles), it is expected that the combination of phosphorous, calcium and fluoride with the nanoparticle is sufficiently durable for at least a material portion of them to be delivered by the nanoparticle to a carious lesion. It is also expected that the addition of a different multivalent cation, for example a different divalent or trivalent cation or alkaline earth metal ion, could similarly increase the retention of anionic active agents such as fluoride, though without the potential benefit of adding calcium.

The nanoparticle might enter the carious lesion through pores in the lesion or stay on the outside of the lesion. Optionally, the teeth may be cleaned to remove plaque and/or the dental pellicle, for example by patient brushing or cleaning by a dental hygienist, before or while applying the nanoparticles to improve access to a carious lesion. As the nanoparticles break down in saliva while near or inside of the lesion, the phosphorous and calcium and/or fluoride may diffuse into the tooth and can deposit or optionally react, with or without additional elements from the tooth or saliva, to form minerals in the tooth. It is also possible that already formed minerals, for example calcium phosphate, calcium-hydroxyapatite or fluorapatite, present within the nanoparticles can act as seed crystal or bio-active agents that fill parts of the lesion or are incorporated into additional minerals produced in the tooth.

Optionally the nanoparticle has a zeta potential of at least +2.0 mV, for example between +2.0 mV and +10.0 mV at all pH values of about 7.0 or less or at all pH values of about 5.5 or less. In some examples, the nanoparticles have a positive zeta potential in acidic solutions but a negative zeta potential under neutral or basic conditions, i.e. pH of 7.0 or more. For example, the zeta potential of the nanoparticles may be at least +2.0 mV at all pH values of about 5.5 or less but negative at pH values of 7.0 or more. Since the pH of saliva in the mouth is roughly neutral (typically about 7.4), but the pH in or near an active carious lesion is typically acidic (typically about 4-5), nanoparticles that have a positive zeta potential only in acidic conditions may be even more selectively targeted to active carious lesions than nanoparticles that have a positive zeta potential even under neutral or mildly basic (i.e. pH of 7.0 or more) conditions. The nanoparticles are administered to teeth, for example as a dispersion used in a rinse or mouthwash, which optionally may include diagnostic fluorescent nanoparticles, or in a gel or paste applied to the teeth, or in toothpaste.

The nanoparticles may have a size of up to 2500 nm but preferably have a size of 1000 nm or less. The term "nanoparticles" as used herein is not limited to particles having a size of 100 nm or less as in the IUPAC definition but also includes larger particles, for example particles up to 2500 nm, or up to 1000 nm, for example in their largest dimension or in the diameter of a sphere of equivalent volume. Optionally, the nanoparticles may have a mean or average size as determined by peak intensity of a DLS plot, the z-average of a DLS measurement or the mean or D50 of an NTA measurement, in the range of about 100 nm to about 700 nm, about 100 nm to about 600 nm, or in the range of about 100 nm to about 500 nm, or in the range of about 200 nm to about 500 nm, or in the range of about 100 nm to about 400 nm. As mentioned above, particles in these size ranges will be called nanoparticles, which is consistent with common usage of that word in North America particularly for particles less than 1000 nm in size. However in other parts of the world, and according to IUPAC definition, particles larger than 100 nm in size may alternatively be called microparticles.

Biopolymers, for example polysaccharides and proteins, and in principle any other biopolymer, and mixtures thereof, may be the biopolymer used in these processes. Any starch, for example waxy or dent corn starch, potato starch, tapioca starch, dextrin, dextran, starch ester, starch ether, carboxymethyl starch (CMS), and in principle any other starch or starch derivative, including cationic or anionic starch, and mixtures thereof, may be the biopolymer used in these processes. Any polysaccharide, cellulosic polymer or cellulose derivative, for example microcrystalline cellulose, carboxymethyl cellulose (CMC), any nanofibrillar cellulose (CNF), nanocrystalline cellulose (CNC), or cellulose ester, cellulose ether, and in principle any other polysaccharide, cellulose or cellulose derivative, and mixtures thereof, may be the biopolymer used in these processes. Proteins, for example zein (corn protein), casein (milk) or soy protein, and in principle any other protein or modified protein, and mixtures thereof, may be the biopolymer used in these processes.

Optionally, the nanoparticles may be prepared by a phase inversion emulsion process as described in U.S. Pat. No. 6,755,915, Method for the Preparation of Starch Particles. In this method starch particles are prepared in a two-phase system comprising steps of a) preparation of a first phase comprising a dispersion of starch in water, b) preparation of a dispersion or emulsion of the first phase in a second liquid phase, c) crosslinking of the starch present in the first phase, d) separating the starch particles thus formed. In some examples the second phase consists of a hydrophobic liquid and step b) consists in forming an oil-in-water emulsion. In some examples the second phase consists of a water-miscible non-solvent for starch.

The nanoparticles are stable in dry form. If stored wet, in a closed container, a sterile 5% w/w aqueous dispersion of cationic-mineral containing starch nanoparticles, or non-sterile aqueous dispersion stabilized with a citric acid/potassium sorbate or other food-grade biocide, may be prepared. However, the biocide might not be required. There are some indications of stability without biocide, but it is not yet known whether the nanoparticles have bacteriostatic or bactericidal properties. Nanoparticles containing fluoride appear to have bacteriostatic or bactericidal properties.

The nanoparticles can be combined with one or more supplemental carriers (i.e. water, excipients or extenders etc.) that are toxicologically and functionally acceptable to create a composition that can be administered to the mount of an animal or person. The composition may be, for example, a mouth rinse, dentrifice, gel, varnish, paint, toothpaste, tooth powder or mouthwash. The carriers can be selected from the usual components of one or more of these compounds. For example, the carriers may be one or more of water, alcohols, surfactants, emulsifiers, foaming agents, abrasives, humectants, viscosity modifiers, tackifiers, film-formers, plasticizers, diluents, pH modifiers, sweeteners, flavors, coloring agents and preservatives. For example, the nanoparticles can be used in a rinse or mouthwash that is swished in the mouth and then suctioned and/or rinsed, at home or in a dental clinic. Alternatively, the nanoparticles can be in a toothpaste administered by brushing the enamel surface at home, or as a paste or gel applied by a hygienist. After being introduced into a mouth, the nanoparticles adhere to plaque or the surface of caries and may travel inside of active carious lesions by passing through the porous surface of the lesion.

The nanoparticles can be used, for example, without, or at least without an effective amount of, any additional oral care active ingredient such as an added anticaries agent or remineralizing agent. In particular, the nanoparticles can be used without adding effective amounts of any of the oral care active ingredients described in United States Patent Application Publication Pub. No. US 2017/0112949 A1 (also published as International Publication Number WO 2017/070578, Detection and Treatment of Caries and Microcavities with Nanoparticles). For example, the nanoparticles can be used without adding, during or after formation of the nanoparticle, one or more of a) a fluoride-containing active ingredient, b) a calcium-containing component, c) a calcium and phosphate containing compound and d) amine fluoride, casein phosphopeptide, phosphoprotein and equivalents and combinations thereof. In this case, the nanoparticle is believed to be effective due to the presence of one or more phosphate-containing, or starch and phosphate-containing, compounds that are introduced by the addition of crosslinker or created in the reaction of the crosslinker and starch. Without intending to be limited by theory, although phosphate alone does not create mineral compounds, the phosphate in the nanoparticle may react with calcium in saliva or other elements, ions or compounds in the mouth to create mineral compounds on or in a tooth or to help nucleate crystal formation within the white spot or active pre-cavity lesion.

Other two-phase emulsions, for example water and alcohol or hexane, might be used. However, the oil phase helps achieve a high loading of non-oil soluble active agents in the nanoparticle. The oil may be a food grade mineral oil, or other, preferably food grade, oils such as sunflower oil or olive oil. A surfactant, for example Tween 85, is also used.

The transition temperature may vary depending on the water to oil ratio, the type of oil, and the type and amount of surfactant.

The following examples are provided to illustrate various embodiments and to provide further enabling disclosure but are not intended to limit any claimed invention.

Example 1—Procedure Used for the Preparation of Starch Nanoparticles without Cationization in the Emulsion In a 1 L plastic beaker 30 g of native waxy corn starch was dispersed into 600 g water along with 16.6 g of NaCl to produce a white suspension of granules. The dispersion was mixed using a Silverson ultra-high shear dissolver agitator at 6500 rpm. 7.5 g of 50% NaOH was added while mixing. The mixer was turned up to 8000 rpm and the temperature of the mixture increased from 22 to 52° C. in ~20-30 minutes; at 41-42° C. the mixture became transparent; light microscopy of a small droplet placed on a glass slide showed a small fraction of starch granule fragments persisted (with birefringence under cross polarizers). At 52° C. all granule fragments were cooked out in the caustic solution (NaOH serves the dual purpose of cooking out the starch at lower temps, and as catalyst for the subsequent crosslinking reaction with STMP). pH paper showed a pH~13-14. Microscopy showed the final starch solution was fully cooked.

The starch solution was cooled to 19° C. and divided into two equal portions of ~320 g of liquid; a target of 8.75 g of Tween 80 was intended, or 29 g of a 30% paste in water, but only 18.53 g was added (all that was left) to one of the two solutions.

Next 300 g (=360 mL; density=0.833) of paraffin oil was added to solution 1; mixing was started at 3:20 pm.

The droplet size was checked with light microscopy.

| Time | Temp (° C.) | RPM | Observations |
|---|---|---|---|
| 3:20 | 22 | 5500 | Oil mixing in OK |
| 3:22 | 25 | 5500 | Dispersion noticeably whitens more |
| 3:24 | 29 | 5500 | O/W to W/O phase transfer has likely occurred |
| 3:29 | 36 | 7500 | |
| 3:44 | 48 | 7500 | |
| 3:47 | 52 | 9000 | Add 1.5 g TSTP |
| 3:48 | 54 | 9500 | |
| 3:55 | 64 | 9500 | |
| 3:56 | 65 | 8500 | |
| 4:06 | 71 | 8500 | |
| 4:14 | 73 | 8500 | |
| 4:48 | 75 | 8500 | End of mixing; cool and neutralize |

The final product was a beautiful white suspension. The final mixture was transferred to capped PE bottle, cooled to <45° C. with cold tap water, then transferred back to the 1 L plastic beaker, mixed using the Silverson mixer, and ~300 mL of water was added; a pH probe was mounted and the pH was adjusted from 11.6 to 8.52 using 12 pipette squirts (about 1 mL each) of 1 N HCl. After neutralizing the suspension was broken (no longer stable).

Example 2—Production of Nanoparticles, Optionally with Fluoride and/or Calcium, without Cationization in the Emulsion Cooked 1 L of a 4.68 wt. % starch solution at 55° C. for 2 hrs at pH 13 containing 0.3-0.6 M NaCl or NaF and leave to cool. Adjust to a pH of 13 obtained by adding NaOH pellets to the water. Alternatively, disperse 60 g or thermo-mechanically processed starch (or other cold water soluble starch) in 400 mL deionized water containing 10 g NaCl or molar equivalent of NaF. Either method produces a water phase Disperse 35 g of Tween 85 in 500 g (600 mL) of paraffin oil to produce an oil phase.

Add 400 g of starch solution or dispersion (water phase) to the oil phase.

Homogenize the mixture using a Silverson mixer, keeping track of the temperature.

Once phase inversion occurs, typically when the temperature is about 50° C., add dry STMP powder if using cooked starch or STMP and 0.95 g NaOH in 3 mL water if using thermo-mechanically processed starch.

Allowed reaction to proceed for 1-4 hr.

Add 200 mL of water containing 3 g 37% HCl for neutralization (=1.5M).

Take a small sample, dilute with 3-5× the volume with water, and check the pH using a pH meter. The target pH is 8.0+/−0.5. Adjust pH if necessary.

Optionally add dry $CaCl_2$) powder to remaining sample (while mixing) and mix for 10 mins.

Allow the oil/water emulsion to settle.

Let the dispersion settle without agitation (for example stored in a refridgerator over a weeked). Decanted off a supernatant above any free calcium-phosphate precipitate. Precipitate nanoparticle in the supernatant with ethanol. Wash and filter the nanoparticles using Büchner filtration three times (3×) with ethanol to remove surfactant.

Redisperse the nanoparticles in water and purify by centrifugation or in a separatory funnel (repeat three times) to remove excess oil.

Perform dialysis to remove free phosphate and chloride salts (6 days) and/or centrifuge at 4000 RPM for 1 minute to remove large aggregates of precipitate (i.e. $CaPO_4$) unbound to starch. Freeze dry the sample to recover product nanoparticles.

Example 3—Production of Nanoparticles, Optionally with Fluoride and/or Calcium, with Cationization in the Emulsion Combine water, starch, sodium hydroxide, surfactant (Tween 85), and oil (mineral oil or paraffin oil) to mixing vessel. Start mixing with high shear mixer and mix until emulsion is formed ~10 minutes.

Add salt (NaCl) and/or sodium fluoride and/or sodium fluorescein, allow to mix until temperature is >60° C.

To cationize starch, add a mixture of glycidyl trimethyl ammonium chloride (GTAC), DI-water, and 2-propanol and allow to react for about 1 hour (30-90 minutes). Monitor temperature and maintain between 60-75° C. by adjusting high speed mixer mixing rate.

Add STMP to mixture and allow to react/cross-link for about 1-2 hours (30-150 minutes). Monitor temperature and adjust mixing speed to maintain temperature less than 75° C. but greater than 60° C. Measure batch pH, and ensure still basic (about pH 10).

If calcium is desired, add calcium chloride (dihydrate), optionally pre-dissolved in water, and mix for an additional 10 minutes.

Neutralize batch (to pH 6.5-8) by addition of HCl if necessary (samples made with calcium might not require this step).

Allow sample to cool to room temperature and/or refrigerate to facilitate phase separation of emulsion.

Dilute sample about 50:50 with 2-propanol and mix. Centrifuge at 10,000 RPM for 10 minutes to induce multi-phase separation of particles, aqueous/hydrophilic phase, and oil/hydrophobic phase. Isolate precipitated particle phase for further purification. Additional rinsing of particles with 2-propanol can help to remove residual oil from samples.

Optionally (preferable for samples with calcium), re-disperse particles in DI-water by shaking, then centrifuge at 1000 RPM for 1-3 minutes to remove any large precipitates, taking the supernatant to the next step.

Flash-freeze the sample and lyophilize to obtain a dry powder sample of isolated mineral-loaded nanoparticles.

In one example according to the process described above, STMP crosslinked nanoparticles with calcium are made with: 35 g Tween 85; 500 g paraffin oil; 400 g water (initially); 3.125 g NaOH powder; 14.04 g starch; 13.8 g NaCl; 8.58 g GTAC; 7.22 g 70% IPA; 18 g water (for making a mixture with GTAC and IPA); 3.38 g STMP; and, 3.4 g $CaCl_2*2H_2O$.

Example 4—Preparation and Measurements of Nanoparticle Samples with Various Minerals and Active Agents Various samples of cationized nanoparticles were made according to the method in Example 3. The relative amounts of starch and one or more of phosphate, calcium and fluoride added as a reactant are as shown in Table 1. Amounts of these additives are in pph by mol relative to 100 mol of starch AGU. The amount of STMP added while making each sample is one third of the amount indicated in Table 1 to account for the three phosphate groups of each STMP molecule. Fluoride is added by way of sodium fluoride added during the creation of the initial water phase. Calcium is added by way of calcium chloride added to the water in oil emulsion. A negative control (GMB 9) was provided by nanoparticles made without adding any of phosphate, calcium and fluoride. A positive control (GMB 10) was made by dissolution of sodium fluoride in deionised water to a concentration of 116 ppm, which matches 1 hour release data for GMB8 as described below.

TABLE 1

Relative composition of nanoparticle samples GMB1-GMB8 (mols relative to 100 mols of starch AGU)

| Sample | GMB1 | GMB2 | GMB3 | GMB4 | GMB5 | GMB6 | GMB7 | GMB8 |
| --- | --- | --- | --- | --- | --- | --- | --- | --- |
| starch | 100 | 100 | 100 | 100 | 100 | 100 | 100 | 100 |
| phosphate | 9 | 9 | 9 | 3 | 90 | 90 | 90 | 90 |
| calcium | 0 | 4.5 | 0 | 4.5 | 0 | 45 | 0 | 45 |
| fluoride | 0 | 0 | 70 | 70 | 0 | 0 | 70 | 70 |

Calcium release from sample GMB8 and fluoride release from samples GMB7 and GMB8 was tested with and without amylase by a dialysis method. Nanoparticles are dispersed in water and placed within a dialysis membrane tube, and measurements are taken periodically by collecting dialysate collected from outside of the dialysis tubes.

With amylase, sample GMB8 released 11 ppm calcium after 1 hour and 21 ppm calcium after 72 hours. Without amylase, sample GMB8 released 1 ppm calcium after 1 hour and 11 ppm calcium after 72 hours. These results indicate a slow, time-dependent, release of calcium from nanoparticles containing calcium and fluoride.

With amylase, sample GMB7 released 1249 ppm fluoride after 1 hour and 21205 ppm fluoride after 72 hours. With amylase, sample GMB8 released 116 ppm fluoride after 1 hour and 7604 ppm fluoride after 72 hours. Without amylase, sample GMB7 released 1161 ppm fluoride after 1 hour and 21205 ppm fluoride after 72 hours. Without amylase, sample GMB8 released 78 ppm fluoride after 1 hour and 8287 ppm fluoride after 72 hours. These results indicate that there was no apparent impact of amylase on the release time and that both samples show a slow release of fluoride extending beyond one hour. A delayed fluoride release is beneficial since it can allow a larger dosage of fluoride to be provided safely. In a home treatment, a delayed release could also make better use of nanoparticles that become attached to plaque and do not enter the carious lesions. Whereas fluoride released quickly tends to precipitate at the surface of a lesion, fluoride released slowly may be able to enter through the pores of a lesion before precipitating.

Phosphorous, calcium and fluoride release was also tested by dispersing nanoparticles according to some of the samples from Table 1 in containers of deionized (DI) water and measuring the concentration of one of either phosphate, calcium or fluoride in the water at different times up to 2 days. The concentration represents the trend in cumulative release of each compound. Calcium was measured by the Arsenazo III colorimetric method. Inorganic phosphorous was measured by the malachite green colorimetric method. Fluoride was measured by n ion-specific electrode using TISAB II.

GMB4, GMB6 and GMB8 were tested for calcium release. GMB4 and GMB8 each produced about 1 mg/L of calcium in the water after two days. GMB6 produced 3.8 mg/L calcium after 6 hours, 7.8 mg/L calcium after 1 day and 10.2 mg/L calcium after 2 days.

GMB4, GMB5 and GMB7 were measured for fluoride release. GMB4 produced 3.6 ppm fluoride after 1 hour, 40 ppm fluoride after 6 hours, 45 ppm fluoride after 1 day and 51 ppm fluoride after 2 days. GMB5 produced 0.1 ppm fluoride after 2 days. GMB7 produced 4.2 ppm fluoride after 1 hour, 21 ppm fluoride after 6 hours, 29 ppm fluoride after 1 day and 36 ppm fluoride after 2 days.

GMB3 to GMB 8 were tested for inorganic phosphorous release. GMB3 produced 0.49 mg/L phosphorous after 6 hours, 0.55 mg/L phosphorous after 1 day and 0.50 mg/L phosphorous after 2 days. GMB4 produced 0.37 mg/L phosphorous after 6 hours, 0.47 mg/L phosphorous after 1 day and 0.64 mg/L phosphorous after 2 days. GMB5 produced 0.81 mg/L phosphorous after 1 hour, 3.78 mg/L phosphorous after 6 hours, 10.0 mg/L phosphorous after 1 day and 13.6 mg/L phosphorous after 2 days. GMB6 produced 0.17 mg/L phosphorous after 1 hour, 3.41 mg/L phosphorous after 6 hours, 7.29 mg/L phosphorous after 1 day and 9.42 mg/L phosphorous after 2 days. GMB7 produced 0.24 mg/L phosphorous after 1 hour, 2.14 mg/L phosphorous after 6 hours, 4.62 mg/L phosphorous after 1 day and 6.29 mg/L phosphorous after 2 days. GMB8 produced 0.43 mg/L phosphorous after 1 hour, 4.59 mg/L phosphorous after 6 hours, 5.39 mg/L phosphorous after 1 day and 6.32 mg/L phosphorous after 2 days.

The average size of the various samples from Table 1 was determined by nanoparticle tracking analysis and dynamic light scattering. The numerical average (mean) size of the particles from NTA analysis and the Z-average (intensity based) size from DLS measurements are provided in Table 2. The NTA measurements are believed to be more accurate due to the polydisperse nature of at least some of the samples. Polydisperse samples are difficult to measure by intensity-based DLS measurements and the Z-average measurements are skewed towards larger particle sizes.

TABLE 2

| Size of nanoparticles | | | | | | | | |
|---|---|---|---|---|---|---|---|---|
| Sample | GMB1 | GMB2 | GMB3 | GMB4 | GMB5 | GMB6 | GMB7 | GMB8 |
| NTA size (nm) | 525 | 385 | 409 | 477 | 186 | 245 | 148 | 313 |
| DLS size (nm) | | | | | 316 | 756 | 315 | 341 |

Figure 2:
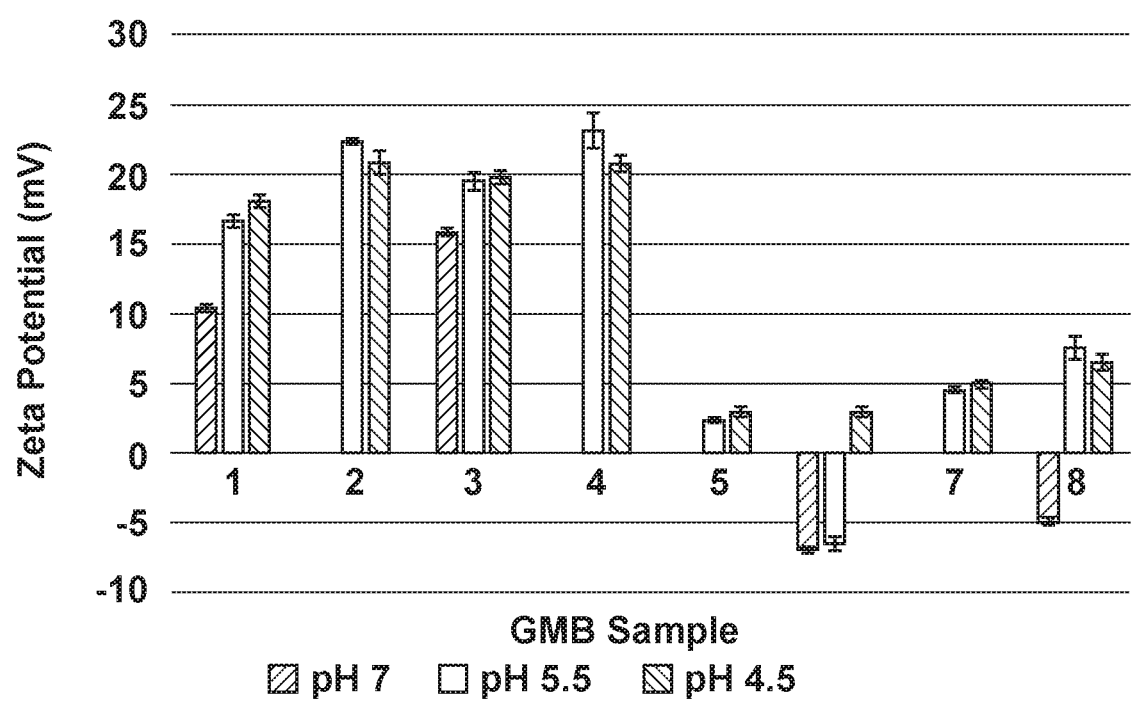
FIG. 2 is a chart showing zeta potential values of nanoparticles made according to the process of FIG. 1 at different pH values.

FIG. 2 shows zeta potential measurements for the samples of Table 1 at different pH values. Samples GMB1 to GMB4, with less phosphorous, are cationic at all pH values tested. Samples GMB6 and GMB8 are cationic at some pH values but anionic at pH 7. It is expected, due to the similar phosphorous content, that samples GMB5 and GMB7 are also anionic at pH 7. This change in charge indicates the potential for "smart" (i.e. pH-triggered) targeting of samples GMB5-GMB8 wherein they would only be electrostatically attracted to a negatively charged lesion if the lesion has bacteria actively producing acidic conditions in or near the lesion, while also potentially reducing attraction to proteins or non-specific cellular binding before reaching the lesion. Alternatively, if the nanoparticles are used without first cleaning the teeth (as in a treatment used at home rather than in a dental office procedure), samples GMB5-GMB8 are less likely to be attracted to plaque or organics material in the mouth that is not near a carious lesion which may be negatively charged but at neutral pH. Optionally, the degree of cationization of samples GMB1 to GMB4 could be reduced since a zeta potential in the range of +2 to +10 mV is sufficient for targeting to carious lesions or plaque, or to make samples that are cationic only in acidic conditions.

Example 5—Remineralization Using Non-Cationized Nanoparticles

Nanoparticles were prepared generally as described in Example 2 using thermo-mechanically processed starch as the starting material to avoid the step of dissolving native starch granules. The nanoparticles had 20 mM of $Ca^{2+}$. Based on TEM images, the nanoparticles appear to have sizes in the range of 200-500 nm and the Z-average size measured by DLS is about 380 nm. One batch of nanoparticles (GM 6) was prepared with NaCl. Another batch of nanoparticles (GM 6 F−) was prepared with NaF in pace of NaCl.

Six enamel slivers were prepared with a demineralized area on each sliver. Three slivers were treated with each of nanoparticles GM 6 and GM 6 F− and the results for each nanoparticle were averaged. The slivers were immersed in dispersions of the nanoparticles for 38 days. Surface VMHN measurements were taken at multiple times up to day 16 and then again on day 38. The results for GM 6 F− showed a generally linear increase in hardness from about 75 to about 165 over the first 16 days and a further increase in hardness to over 200 on day 38. The results for GM 6 showed a generally linear increase in hardness from about 75 to about 100 and a decrease in hardness to about 75 on day 38. The decrease in hardness on day 38 for GM 6 is believed to be the result of bacterial growth on the starch whereas the fluoride of GM 6 F− makes those nanoparticles antibacterial. Confocal microscopy of cross section of the demineralized area in the sample treated with GM 6 F− showed a decrease in the lesion depth from 38 μm to 3 μm over the course of the trial.

Example 6—Remineralization with Cationized Nanoparticles

Enamel slivers were prepared with a demineralized area on each sliver according to a lactic acid and carboxymethylcellulose (CMC) gel protocol as described in Featherstone et al. (Featherstone, J. D. B. and Mellberg, J. R. (1981) *Relative rates of progress of artificial carious lesions in bovine, ovine and human enamel*. Caries Res. 15, 109-114). The enamel slivers were partially protected with an impermeable varnish and subsequently treated with various nanoparticle formulations as described in Table 1 while exposed to continued lactic acid and CMC demineralization for 20 days. The nanoparticle treatment consisted of contacting the slivers with one of the nanoparticle samples for 4 minutes, 4 times daily, over the course of the 20 days. The continued lactic acid and CMC demineralization protocol included a 4-hour period of acid cycling in the aforementioned lactic acid and CMC demineralization solution and immersion in an amylase-containing artificial saliva solution when the slivers were not immersed in the lactic acid and CMC demineralization solution.

A VMHN value of 300 or more is associated with healthy enamel. A VMHN of less than 100 is associated with soft demineralized enamel. Table 3 gives the average starting and ending VMHN for enamel samples treated with each nanoparticle formulation and the controls in the trial. As indicated by the controls, the trial conditions produce a decrease of VMHN over time. However, all of the samples GMB1 through GMB8 provided improved results relative to both controls. Further, treatment with samples GMB1, GMB4, GMB5, GMB7 and GMB8 showed an increase of VMHN after 20 days.

It is interesting to note that GMB5 produced good results but does not have fluoride or calcium. Without intending to be limited by theory, it is possible that the phosphate groups of this sample draw calcium from saliva to produce precipitates in the tooth.

Example 7—Treatment of Dentinal Hypersensitivity

Two oral gels were formulated with nanoparticles according to sample GMB8 described above. The gels were stabilized with propylene glycol and thickened with food grade gelatin. Formulation 1 had 25% w/w of the nanoparticles. Formulation 2 had 5% w/w of the nanoparticles. The effect of the two gel formulations containing on dentinal hypersensitivity was determined by applying the formulations to dentine discs and measuring a change in dentinal permeability as indicated by measurements of hydraulic conductance. Since it is believed that dentinal hypersensitivity (DH) involves neural stimulation by fluid flow within dentinal tubules, occlusion of the tubules as indicated by a change in hydraulic conductance indicates a potential treatment of DH.

The dentine discs were cut from extracted human third molar teeth. Each tooth was cut transversely just below the widest part of the tooth, then sectioned to produce dentine discs with a thickness of 0.5 mm. Each disc has a minimum 4 mm diameter. The discs are polished with carbide paper until flat and then acid etched to remove any smear layer produced during the cutting and polishing procedures. The disc is placed in a tube and water is applied against the disc at a pressure of 1 psi. The volume of water passing through the disc in 5 minutes is measured. The test is performed before and after treatment of the disc with the nanoparticles and again after storing the samples for 24 hours in artificial saliva. The treatments are done by: soaking the discs in artificial saliva for 30 minutes; applying one of the gel formulations to each disc; rubbing the gel on the dentin surface for 2 minutes; waiting for 10 minutes; and, rinsing the discs.

Samples treated with nanoparticles according to formulation 1 showed a reduction in flow (relative to flow before treatment) of about 40% immediately after application of the nanoparticles and after 24 hours. Samples treated with nanoparticles according to GMB8 formulation 2 showed a reduction in flow of about 75% immediately after application of the nanoparticles and after 24 hours.

Example 9—Fluorescent Nanoparticles

Sodium fluorescein and calcium chloride were added to a vial of water at a pH of about 10. A precipitate of calcium fluorescein formed at the bottom of the vial.

Nanoparticles were made according to the process described in Example 3 with: 74 g Tween 85; 1121 g mineral oil; 842 g water (initially); 13 g NaOH powder; 39 g starch; 29 g NaCl; 0.75 g sodium fluorescein; 25 g GTAC; 20 g 70%

TABLE 3

| Initial and 20 day VMHN | | | | | | | | | | |
|---|---|---|---|---|---|---|---|---|---|---|
| Sample | GMB1 | GMB2 | GMB3 | GMB4 | GMB5 | GMB6 | GMB7 | GMB8 | GMB9 | GMB10 |
| Initial VMHN | 145 | 139 | 126 | 111 | 101 | 114 | 120 | 109 | 112 | 116 |
| 20 day VHMN | 171 | 132 | 96 | 179 | 178 | 87 | 158 | 143 | 24 | 24 |

IPA; 50 g water (for making a solution with GTAC and IPA); 28 g STMP; and, 27 g $CaCl_2 \cdot 2H_2O$ pre-dissolved in 200 g water.

The resulting nanoparticles had a yellow-orange color indicating the presence of fluorescein in the nanoparticles. The nanoparticles may be used for the purposes described for starch nanoparticles reacted with fluorescein amine coupled onto the starch nanoparticles via EDC-NHS chemistry as described in described in United States Patent Application Publication Pub. No. US 2017/0112949 A1 (also published as International Publication Number WO 2017/070578), Detection and Treatment of Caries and Microcavities with Nanoparticles. However, the method of making fluorescent nanoparticles described herein is less expensive and the nanoparticles simultaneously deliver beneficial agents to the caries.

International Publication Number WO 2017/070578, Detection and Treatment of Caries and Microcavities with Nanoparticles, is incorporated by reference. International Publication Number WO 2013/081720 A1, Aptamer Bioconjugate Drug Delivery Agent, is incorporated herein by reference. All of the patent publications and other publications mentioned herein are incorporated by reference.

The term "preferable" or variants thereof indicates that something is preferred but optional. Words such as "may" or "might" are meant to include the possibility that a thing might, or might not, be present. The words "fluorine" and "fluoride" are intended to include whatever form of fluorine may be present. For example, the word "fluoride" is not intended to require the presence of distinct, soluble $F^-$ ions, but could be satisfied by the presence of fluorine in the insoluble part of a compound such as calcium fluoro apatite, in combination with a salt such as $CaF_2$ whether the salt is in a dissolved or precipitated state, or combined with the nanoparticle in any other way.

We claim:

1. Nanoparticles comprising starch and phosphorous, wherein the nanoparticles have a positive zeta potential at a pH of 5.5 or less, wherein the nanoparticles have a mean or average size in the range of 100-500 nm as determined by the Z-average size in dynamic light scattering (DLS) or as determined by the mean size in nanoparticle tracking analysis (NTA).

2. The nanoparticles of claim 1 comprising one or more of fluoride, fluorescein or calcium.

3. The nanoparticles of claim 1 comprising fluoride and calcium.

4. The nanoparticles of claim 1 having a negative zeta potential at a pH of 7.0 or more.

5. The nanoparticles of claim 1 incorporated into an aqueous dispersion, a gel or a paste.

6. The nanoparticles of claim 1 wherein the phosphorous is present in starch-phosphate compounds and/or dangling phosphates.

7. A method of making nanoparticles of claim 1 comprising the steps of,
    preparing a first phase comprising a solution or dispersion of starch in water;
    preparing a dispersion or emulsion of the first phase in a second liquid phase such as an oil phase;
    adding one or more of (a) one or more multi-valent cations, and (b) one or more starch cationizing agents to the first phase; and,
    crosslinking the starch in the first phase with a phosphate crosslinker.

8. The method of claim 7 comprising adding an anionic active agent to the first phase, wherein the anionic active agent comprises fluoride.

9. The method of claim 7 comprising adding an anionic active agent to the first phase, wherein the anionic active agent comprises fluorescein.

10. The method of claim 7 wherein the one or more multivalent cations comprises calcium.

11. The method of claim 7 comprising adding one or more starch cationizing agents.

12. The method of claim 7 wherein the crosslinker comprises sodium trimetaphosphate.

13. A method of filling a tooth or supporting the remineralization of a tooth comprising administering nanoparticles of claim 1 fortified with calcium and/or fluoride to the tooth.

14. The method of claim 13 wherein the nanoparticles are dispersed in a liquid, paste or gel carrier and applied to the tooth.

15. The method of claim 14 wherein the nanoparticles are applied to a tooth after or while cleaning a pellicle and/or plaque from the tooth.

16. The method of claim 13 wherein the nanoparticles comprise a mineral, for example calcium phosphate, fluorapatite or calcium hydroxyapatite.

* * * * *